(12) United States Patent
Ross

(10) Patent No.: US 6,605,643 B1
(45) Date of Patent: Aug. 12, 2003

(54) INSECT REPELLENT EMULSIONS

(75) Inventor: Jamie S. Ross, Putnam, CT (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 08/977,326

(22) Filed: Nov. 24, 1997

Related U.S. Application Data
(60) Provisional application No. 60/032,054, filed on Nov. 26, 1996.

(51) Int. Cl.$^7$ .......................... A01N 37/18; A01N 25/02
(52) U.S. Cl. .......................... 514/617; 424/59; 424/60; 424/405; 424/406; 424/DIG. 10; 514/532; 514/919
(58) Field of Search .......................... 424/405–10, 407, 424/409, 59, 60, 78.02, 78.03, 78.17, 78.31, DIG. 10; 514/617, 159, 532, 919, 534, 537

(56) References Cited

U.S. PATENT DOCUMENTS

| | | | | |
|---|---|---|---|---|
| 2,435,005 A | * | 1/1948 | Huppke et al. | 424/DIG. 10 |
| 4,353,962 A | | 10/1982 | Himel et al. | 428/407 |
| 5,204,090 A | | 4/1993 | Han | 424/59 |
| 5,518,712 A | * | 5/1996 | Stewart | 424/59 |
| 5,916,541 A | * | 6/1999 | Stewart | 424/59 |

FOREIGN PATENT DOCUMENTS

| | | |
|---|---|---|
| EP | 0 085 334 A | 8/1983 |
| EP | 0 265 087 A | 4/1988 |
| EP | 0 274 574 A | 7/1988 |
| EP | 0 275 085 A | 7/1988 |
| GB | 2222949 A | 3/1990 |
| WO | WO 89/06904 | 8/1989 |
| WO | WO 94/00104 | 1/1994 |
| WO | WO 95/19161 | 7/1995 |
| WO | WO 97/42933 | 11/1997 |
| WO | WO 97/49380 | 12/1997 |

OTHER PUBLICATIONS

D. Hartley et al., Eds., "DEET," *The Agrochemicals Handbook*, The Royal Society of Chemistry, London, 1983.

* cited by examiner

*Primary Examiner*—Neil S. Levy
(74) *Attorney, Agent, or Firm*—Robert A. Franks

(57) ABSTRACT

The invention relates to storage stable insect repellent emulsion formulations containing N,N-Diethyl-m-toluamide, together with water, a film-forming polymer and an emulsifier-emulsion stabilizer.

8 Claims, No Drawings

INSECT REPELLENT EMULSIONS

CROSS-REFERENCE TO RELATED APPLICATIONS

This application claims the benefits under 35 U.S.C. §119(e) of provisional application No. 60/032,034 filed Nov. 26, 1996.

INTRODUCTION TO THE INVENTION

The present invention relates to fluid formulations containing the insect repellent agent DEET, and more particularly to emulsion formulations thereof.

Man has long used various chemical agents to reduce attacks by bothersome insects, such as mosquitoes, flies, ticks, wasps and bees. The most widely used insect repellent agent at the present time is N,N-Diethyl-m-toluamide, frequently called "DEET." DEET is an unctuous, somewhat hygroscopic, light-sensitive, oily material having a very high solvency for other water-insoluble materials. It has some notoriety for being difficult to emulsify, so is frequently used in concentrated form or formulated as an aerosol spray or dilute solution, or in solid or semi-solid form such as in a stick. To repel insects, one applies DEET or formulations containing up to about 100% DEET to clothing and exposed skin.

However, humans usually prefer the feel of aqueous materials on their skin. In the cosmetic and medical fields, it has been found that oily materials can be made more pleasing by their incorporation into oil-in-water emulsions. Since the droplets of insoluble material are completely surrounded by the aqueous phase, the sensation to the skin is essentially one of applying aqueous materials. Emulsions are also easier to apply evenly to skin, than are solutions, sprays and gelled materials in stick form. DEET, however, does not typically form emulsions having commercially required stability, and it is quite undesirable to require users to mix the separated phases before using products.

SUMMARY OF THE INVENTION

The invention includes a water-in-oil insect repellent emulsion comprising an effective amount of N,N-Diethyl-m-toluamide, water, a film-forming polymer and an emulsifier-emulsion stabilizer.

The emulsion has commercially acceptable storage stability and a pleasing feel when applied to the skin.

DETAILED DESCRIPTION OF THE INVENTION

In this application, all references to "percent" shall mean percent by weight, unless the context clearly indicates otherwise. Many of the formulation components (surfactants, emulsion stabilizers, film-formers, etc.) are identified herein by their names as given in the monographs of J. A. Wenninger et al., Eds., *CTFA Cosmetic Ingredient Handbook, Second Edition,* The Cosmetic, Toiletry and Fragrance Association, Inc., Washington, D.C., 1992.

DEET is commercially available in the form of a technical concentrate which contains at least about 95% DEET. The remaining 5% or less comprises moisture and isomers other than the meta-toluic isomer, which other isomers are considered to also have some insect repellent activity, plus small amounts of impurities which are artifacts of the manufacturing process employed. For simplicity, a recitation herein of DEET concentration shall ignore the other components of the concentrate: "10% DEET" shall indicate that a formulation contains 10% of a commercial technical concentrate.

The emulsions of the present invention contain DEET, at about 5 to about 25 percent, together with water, a film-forming polymer and an emulsifier-emulsion stabilizer. In some instances, a supplemental emulsifying agent may be useful as a formulation component.

Suitable supplemental emulsifiers include, without limitation, the surfactants sorbitan stearate, stearic acid, sorbitan oleate, cetyl alcohol, glyceryl oleates, glyceryl stearates, sorbitan sesquioleate, DEA-cetyl phosphate (the diethanolamine salt of cetyl phosphate), Oleth-20 [the polyethylene glycol ether of oleyl alcohol having the formula $CH_3(CH_2)_7CH=CH(CH_2)_7CH_2(OCH_2CH_2)_nOH$, where n has an average value of 20], PEG-8 distearate [the polyethylene glycol diester of stearic acid having the formula $CH_3(CH_2)_{16}C(O)(OCH_2CH_2)_nOC(O)(CH_2)_{16}CH_3$ where n has an average value of 8], PEG-8 oleate [the polyethylene glycol ester of oleic acid having the formula $CH_3(CH_2)_7CH=CH(CH_2)_7C(O)(OCH_2CH_2)_nOH$ where n has an average value of 8], PEG-2 stearate [the polyethylene glycol ester of stearic acid having the formula $CH_3(CH_2)_{16}C(O)(OCH_2CH_2)_nOH$ where n has an average value of 2], Polysorbate 20 (a mixture of laurate esters of sorbitol and sorbitol anhydrides, consisting predominately of the monoester, condensed with approximately 20 moles of ethylene oxide), Polysorbate 60 (a mixture of stearate esters of sorbitol and sorbitol anhydrides, consisting predominately of the monoester, condensed with approximately 20 moles of ethylene oxide), Polysorbate 80 (a mixture of oleate esters of sorbitol and sorbitol anhydrides, consisting predominately of the monoester, condensed with approximately 20 moles of ethylene oxide), propylene glycol stearate, sodium laureth sulfate, sorbitan sesquioleate and many others known in the art. In general, and keeping in mind that there are numerous exceptions to this statement, oil-in-water emulsions are prepared using emulsifiers having hydrophilic-lipophilic balance ("HLB") values about 8 to about 18. Combinations of emulsifiers may be used, and frequently will be found to impart a greater emulsion stability than single emulsifiers. When combinations are used, all of the individual HLB values may not always be within the above range, but the overall HLB value usually will be. In general, when present, the emulsifier component will amount to about 0.1% to about 10% of the formulation.

A film-forming polymer is present to provide a continuous film upon skin application and water resistance to the formulation. Water resistance may assist in obtaining an enhanced duration of action for the insect repellent agent. This would be particularly desirable for users participating in water-related activities, such as fishing, water skiing, swimming or activities which may incidentally involve water contact, or for users who are engaged in strenuous sports or work activities and perspire heavily. Useful film formers include: copolymers of octadecene and maleic anhydride; copolymers of 1-triacontane and vinyl pyrrolidone; acrylates/octylacrylamide copolymer; acrylates/PVP copolymer (a copolymer of 1-vinyl-2-pyrrolidone and one or more monomers of acrylic acid, methacrylic acid and one of their simple esters); acrylates/acrylamide copolymer; acrylates/VA copolymer (a copolymer of vinyl acetate and one or more monomers of acrylic acid, methacrylic acid and one of their simple esters); ethylene/maleic anhydride copolymer; polyisobutene; polyvinyl alcohol; PVP/eicosene copolymer (a polymer of vinylpyrrolidone and eicosene monomers); starch/acrylates/acrylamide copolymer; and hexanedioic acid polymers. Such ingredients will generally be present in a formulation in amounts about 0.1% to about 5%.

Also required in the formulation is an emulsifier-emulsion stabilizer, such as an acrylates/C10–30 alkyl acrylate crosspolymer, carbomer, (a homopolymer of acrylic acid crosslinked with an allyl ether of pentaerythritol or an allyl ether of sucrose) methyl vinyl ether/maleic anhydride copolymer or a triethanolamine salt of stearic acid. Suitable acrylates/C10–30 alkyl acrylate crosspolymer materials are commercially available from B.F. Goodrich Chemicals, Akron, Ohio under the trade names PEMULEN® TR-1 and TR-2, or CARBOPOL®. The concentration of emulsifier-emulsion stabilizer in the formulation will typically be about 0.01% to about 5%. In some formulations, it has been found that the concentration of the emulsion stabilizer PEMULEN TR-2 should not exceed about 0.8%, to avoid viscosity increases which adversely affect emulsion preparation and handling.

Other components, while not required, are commonly included in skin care products to enhance the feel of the material upon application, to treat dry skin conditions and/or to protect the formulation against microbial contamination. These include emollients, fragrances, preservatives, vitamins, humectants, skin conditioners, antioxidants and others. Any of such materials may be included as desired, in addition to the required components.

Sunscreening ingredients are also useful optional components of the formulations, when the user desires concomitant protection against excessive ultraviolet radiation exposure. Since the choice of sunscreen active agents is usually limited to those having governmental approvals, those skilled in the art will be aware of acceptable compounds. In the United States, these currently include: aminobenzoic acid; cinoxate; diethanolamine p-methoxycinnamate; digalloyl trioleate; dioxybenzone; ethyl 4-[bis(hydroxypropyl)] aminobenzoate; 2-ethylhexyl 2-cyano-3,3-diphenylacrylate; ethylhexyl p-methoxycinnamate; 2-ethylhexyl salicylate; glyceryl aminobenzoate; homosalate; lawsone with dihydroxyacetone; menthyl anthranilate; oxybenzone; Padimate A; Padimate O; 2-phenylbenzimidazole-5-sulfonic acid; red petrolatum; sulisobenzone; and triethanolamine salicylate. Other active sunscreen ingredients, such as avobenzone, titanium dioxide and phenylbenzimidazole sulfonic acid, are approved for use in many countries and may also be incorporated into the insect repellent formulations of the present invention.

Sunscreening ingredients will be used in sunscreen effective amounts as needed to provide a desired sun protection factor (SPF), which may be measured using at least the essence of the procedure proposed to be established by the United States Food and Drug Administration as Title 21, Code of Federal Regulations, Part 352, Subpart D (Sections 352.70–352.77), which proposal was published in the *Federal Register* on May 12, 1993 at pages 28298–28301. In general, up to about 30 percent sunscreens can be used.

The invention will be further illustrated by the following examples, which are not intended to limit the scope of the invention as defined in the appended claims.

EXAMPLE 1

A storage-stable insect repellent lotion is prepared using the following ingredients:

| Name | * | Percent |
| --- | --- | --- |
| Water | | 41.89 |
| C12–15 alkyl benzoate | C | 21.50 |
| DEET | D | 10.00 |
| Sorbitol, 70% aqueous solution | B | 5.00 |
| Sorbitan oleate | C | 4.00 |
| Sorbitan stearate | C | 3.00 |
| Glyceryl stearate, self emulsifying | C | 3.00 |
| Stearic acid | C | 2.00 |
| Octadecene/maleic anhydride copolymer | C | 2.00 |
| Hydrogenated vegetable oil | C | 2.00 |
| Triethanolamine | B | 1.80 |
| Benzyl alcohol | E | 1.00 |
| Propylparaben | C | 1.00 |
| Fragrance | E | 0.70 |
| Dimethicone | C | 0.40 |
| Methylparaben | C | 0.20 |
| Imidazolidinyl urea | F | 0.20 |
| PEMULEN ® TR-2 | A | 0.10 |
| Vitamin E | C | 0.10 |
| Jojoba oil | C | 0.05 |
| Aloe vera lipoquinone | C | 0.05 |
| Disodium EDTA | B | 0.01 |

* Letter identifies components added during particular process steps

The emulsion is prepared as follows: (1) all but a small portion of the water and the Pemulen TR-2 are mixed to form a clear solution and heated to about 60–65° C.; (2) components identified with a "B" above are sequentially added to the step 1 solution, with mixing to dissolve; (3) all components identified as "C" are mixed, except for the vitamin E, dimethicone and octadecene/maleic anhydride copolymer, to form a solution and heated to about 82–85° C.; (4) the octadecene/maleic anhydride copolymer is added to the step 3 mixture, and dissolved; (5) the step 4 mixture is cooled to about 65–71° C. and the remaining "C" components are added and dissolved; (6) the warm "D" component is added to the warm mixture from step 5 and dissolved; (7) the solution from step 6 is added to the solution from step 2, with sufficient agitation to form an emulsion, and mixing is continued until the emulsion cools to about 49–54° C.; (8) the "E" components are added to the emulsion from step 7, with continued mixing; (9) the remaining water and the "G" component are mixed to form a solution, then added to the emulsion of step 8; and (10) the emulsion is cooled to room temperature and water is added to compensate for evaporative losses during the preparation.

EXAMPLE 2

A storage-stable insect repellent lotion, containing sufficient sunscreen components to provide a waterproof sun protection factor (SPF) of 15, is prepared using the following ingredients and the general procedure of the preceding example:

| Name | Percent |
| --- | --- |
| Water | 42.79 |
| DEET | 10.00 |
| Octyl methoxycinnamate | 7.50 |
| Octyl salicylate | 5.00 |
| Homomenthyl salicylate | 5.00 |
| Sorbitol, 70% aqueous solution | 5.00 |
| Oxybenzone | 4.00 |
| Sorbitan oleate | 4.00 |
| Glyceryl stearate, self emulsifying | 3.00 |

-continued

| Name | Percent |
| --- | --- |
| Sorbitan stearate | 3.00 |
| Stearic acid | 2.00 |
| Hydrogenated vegetable oil | 2.00 |
| Octadecene/maleic anhydride copolymer | 2.00 |
| Triethanolamine | 1.80 |
| Benzyl alcohol | 1.00 |
| Fragrance | 0.70 |
| Dimethicone | 0.40 |
| Methylparaben | 0.20 |
| Imidazolidinyl urea | 0.20 |
| PEMULEN ® TR-2 | 0.10 |
| Propylparaben | 0.10 |
| Vitamin E | 0.10 |
| Jojoba oil | 0.05 |
| Aloe vera lipoquinone | 0.05 |
| Disodium EDTA | 0.01 |

For this emulsion preparation, sunscreen active ingredients are added as "C" components.

EXAMPLE 3

A storage-stable insect repellent lotion, containing sufficient sunscreen components to provide a waterproof SPF of 30, is prepared using the following ingredients:

| Name | * | Percent |
| --- | --- | --- |
| Water | | 57.09 |
| Homomenthyl salicylate | B | 13.00 |
| DEET | D | 10.00 |
| Octyl methoxycinnamate | B | 7.50 |
| Oxybenzone | B | 6.00 |
| Sorbitol, 70% aqueous solution | A | 2.00 |
| Octadecene/maleic anhydride copolymer | C | 2.00 |
| Triethanolamine | A | 1.00 |
| Dimethicone | C | 0.40 |
| Pemulen ® TR-2 | A | 0.30 |
| Fragrance | E | 0.30 |
| Imidazolidinyl urea | F | 0.20 |
| Vitamin E acetate | B | 0.10 |
| Aloe vera lipoquinone | B | 0.05 |
| Jojoba oil | B | 0.05 |
| Disodium EDTA | A | 0.01 |

* Letter identifies components added during particular process steps

The emulsion is prepared as follows: (1) the components identified in the table with an "A" are mixed with all but a small portion of the water, while heating to about 49–55° C. to form a solution; (2) the "B" components are mixed and heated to about 80–82° C., to form a solution; (3) to the step 2 solution are sequentially added the "C" components, with sufficient mixing after each addition to form a solution; (4) the step 3 solution is cooled to about 62–68° C.; (5) the DEET is added to the step 4 solution and thoroughly mixed; (6) the solution of step 1 is agitated to form a vortex and the solution of step 5 is slowly added, to form an emulsion, then mixing is continued as the mixture cools to about 49–52° C.; (7) the fragrance is added to the mixture from step 6 and mixing is continued as the batch cools to ambient temperature; (8) the "F" component is dissolved in the remaining water and added to the mixture of step 7; and (9) sufficient water is added, with mixing, to compensate for evaporative losses during the preparation.

What is claimed is:

1. An insect repellent emulsion composition comprising:
about 5 to about 25 weight percent of N,N-diethyl-m-toluamide;
water;
about 2 weight percent of octadecene/maleic anhydride copolymer;
about 0.1 weight percent of acrylates/C10–30 alkyl acrylate crosspolymer;
about 2 weight percent of stearic acid;
about 1.8 weight percent of triethanolamine; and
a supplemental emulsifying agent comprising at least one of: about 4 weight percent of sorbitan oleate; about 3 weight percent of sorbitan stearate; and about 3 weight percent of glyceryl stearate.

2. The composition of claim 1, comprising about 10 weight percent of N,N-diethyl-m-toluamide.

3. An insect repellent emulsion composition comprising:
about 5 to about 25 weight percent of N,N-diethyl-m-toluamide;
water;
about 2 weight percent of octadecene/maleic anhydride copolymer;
about 0.1 weight percent of acrylates/C10–30 alkyl acrylate crosspolymer;
about 2 weight percent of stearic acid;
about 1.8 weight percent of triethanolamine;
a supplemental emulsifying agent comprising at least one of: about 4 weight percent of sorbitan oleate; about 3 weight percent of sorbitan stearate; and about 3 weight percent of glyceryl stearate; and
a sunscreening effective amount of a sunscreening agent comprising octylmethoxycinnamate, octyl salicylate and homomenthyl salicylate.

4. The composition of claim 3, comprising about 10 weight percent of N,N-diethyl-m-toluamide.

5. An insect repellent emulsion composition comprising:
about 5 to about 25 weight percent of N,N-diethyl-m-toluamide;
water;
about 2 weight percent of octadecene/maleic anhydride copolymer;
about 0.3 weight percent of acrylates/C10–30 alkyl acrylate crosspolymer;
up to about 10 percent by weight of a supplemental emulsifying agent selected from the group consisting of: sorbitan stearate; stearic acid; sorbitan oleate; cetyl alcohol; glyceryl oleates; glyceryl stearates; sorbitan sesquioleate; diethanolamine salt of cetyl phosphate; Oleth-20; a polyethylene glycol diester of Stearic acid having a formula $CH_3(CH_2)_{18}C(O)(OCH_2CH_2)_8)C(O)(CH_2)_{16}CH_3$; a polyethylene glycol ester of oleic acid having a formula $CH_3(CH_2)_7CH=CH(CH_2)_7C(O)(OCH_2CH_2)_8OH$; a polyethylene glycol ester of stearic acid having a formula $CH_3(CH_2)_{16}C(O)(OCH_2CH_2)_2OH$; Polysorbate-20; Polysorbate-60; Polysorbate-80; propylene glycol stearate; sodium laureth sulfate; and mixtures of any two or more thereof; and
a sunscreening effective amount of a sunscreening agent.

6. The composition of claim 5, comprising about 10 weight percent of N,N-diethyl-m-toluamide.

7. The composition of claim 5, wherein the sunscreening agent is selected from the group consisting of: aminobenzoic acid; cinoxate; diethanolamine p-methoxycinnamate; digalloyl trioleate; dioxybenzone; ethyl 4-[bis(hydroxypropyl)] aminobenzoate; 2-ethylhexyl 2-cyano-3,3-diphenylacrylate; ethylhexyl p-methoxycinnamate; 2-ethylhexyl salicylate, glyceryl aminobenzoate; homosalate; lawsone with dihydroxyacetone; menthyl anthranilate; oxybenzone; Padimate A; Padimate O; 2-phenylbenzimidazole-5-sulfonic acid; red petrolatum; sulisobenzone; triethanolamine salicylate; avobenzone; titanium dioxide; phenylbenzimidazole sulfonic acid; and mixtures of any two or more thereof.

8. The composition of claim 5, wherein the sunscreening agent comprises octylmethoxycinnamate, oxybenzone and homomenthyl salicylate.

* * * * *